United States Patent [19]

Doe, Jr.

[11] Patent Number: 4,818,778
[45] Date of Patent: Apr. 4, 1989

[54] RUBBER COMPOSITIONS CONTAINING PHENOL DERIVATIVES OF 1,3,4-THIADIAZOLE

[75] Inventor: Lester A. Doe, Jr., Newtown, Conn.

[73] Assignee: R. T. Vanderbilt Company, Inc., Norwalk, Conn.

[21] Appl. No.: 132,830

[22] Filed: Dec. 7, 1987

Related U.S. Application Data

[62] Division of Ser. No. 46,613, May 7, 1987, Pat. No. 4,734,457.

[51] Int. Cl.$^4$ .................................................. C08K 5/46
[52] U.S. Cl. ........................................ 524/83; 524/571
[58] Field of Search .................................. 524/83, 571

[56] References Cited

U.S. PATENT DOCUMENTS

| 2,850,453 | 9/1958 | Fields | 252/32.7 |
| 3,676,449 | 7/1972 | Song | 260/45.8 |
| 3,960,783 | 6/1976 | Seltzer et al. | 528/211 |
| 4,128,510 | 12/1978 | Richwine | 525/331.1 |

Primary Examiner—Herbert J. Lilling
Attorney, Agent, or Firm—Rasma B. Balodis

[57] ABSTRACT

A process is disclosed for stabilization of natural rubber against oxidative degradation by incorporating therein phenolic derivatives of 3-hydroxymethyl-5-hydroxymethylthio-1,3,4-thiadiazolidine-2-thione and stabilized rubber compositions thereof.

3 Claims, No Drawings

RUBBER COMPOSITIONS CONTAINING PHENOL DERIVATIVES OF 1,3,4-THIADIAZOLE

This is a division of application Ser. No. 07/046,613 filed May 7, 1987, now U.S. Pat. No. 4,734,457.

BACKGROUND OF THE INVENTION

This invention relates to antioxidants for rubber compositions and their use in the stabilization of said compositions. More particularly, the invention relates to rubber compositions that possess a high degree of resistance to the detrimental effects of oxidative aging over prolonged periods of time.

Essentially all types of rubber are known to be susceptible to deterioration resulting from prolonged exposure to atmospheric oxygen. The major cause of deterioration is the attack of oxygen on the olefinic unsaturation bonds contained in rubber. To prevent deterioration, various antioxidants are added depending on the severity of processing and service of the finished article. Thus, there is a need for novel antioxidants which produce commercially acceptable articles. Among the known antioxidants, phenolic type antioxidants are widely used to protect rubber against oxidative effects. However, many of the phenolic antioxidants may be volatilized at high temperature applications.

It has been now discovered that certain phenol derivatives of 1,3,4-thiadiazole prevent the detrimental effect of oxygen on rubber compositions over long periods of time at elevated temperatures.

SUMMARY OF THE INVENTION

In accordance with the invention, there is provided a rubber composition having incorporated therein a 1,3,4-thiadiazole compound selected from the group consisting of (a) compounds of the structural formula

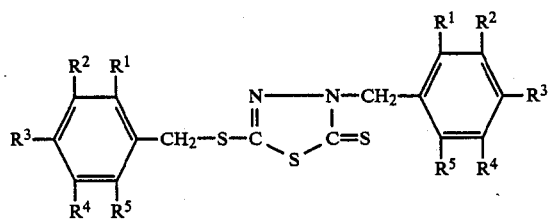

wherein $R^2$ represents t-butyl group, $R^4$ represents $C_{1-4}$-alkyl groups, and $R^1$, $R^3$ and $R^5$ represent hydrogen and hydroxy groups provided that $R^1$ and $R^5$ are hydrogens when $R^3$ is hydroxy and $R^3$ is hydrogen when $R^1$ and $R^5$ are hydroxy groups and (b) reaction products of 4,4'-(1-methylethylidene)bisphenol and 3-hydroxymethyl-5-hydroxymethylthio-1,3,4-thiadiazolidine-2-thione in the molar ratio of 1:1 to 2:1.

Another aspect of the invention is a method of protecting rubber compositions against oxidative deterioration by incorporating therein the above described 1,3,4-thiadiazole compounds.

DETAILED DESCRIPTION OF THE INVENTION

The antioxidants of the invention may be prepared by reacting a phenol with 3-hydroxymethyl-5-hydroxymethylthio-1,3,4-thiadiazolidine-2-thione according to the following reaction scheme

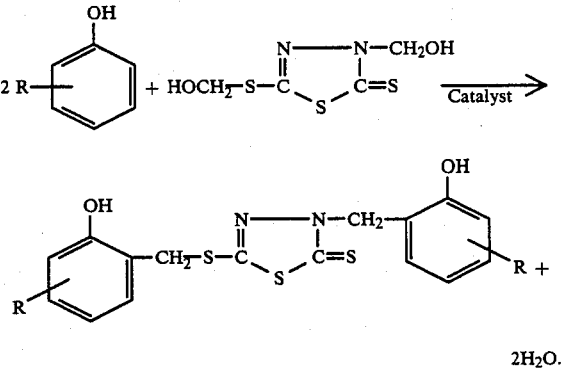

Alternately, the compounds may be prepared by reacting the phenol with 2,5-mercapto-1,3,4-thiadizole and formaldehyde in the presence of an acid catalyst. In both methods, the catalyst may be selected from strong acids such as p-toluenesulfonic acid, sulfuric acid and hydrochloric acid.

The antioxidants of the invention may be incorporated into rubber in the amount of about 0.2 to 5 parts per hundred parts rubber (PHR). The effective amount will depend to some extend on the type and grade of rubber used and on the severity of the deteriorating conditions to which the finished article will be exposed.

Rubber that can be protected with the antioxidants includes natural rubber such as balata and gutta percha rubber in various forms.

The rubber may be of the black variety containing carbon black fillers and of light variety containing inorganic and mineral fillers such as, among others, titanium dioxide, calcium carbonate, silicate minerals, particularly kaolin clay, whiting, talc and wollastonite. Other compounding ingredients may be added as necessary. The following compounding ingredients, among others, are applicable: accelerators, plasticizers, peptizers, lubricants and processing aids.

The data hereinbelow are intended to illustrate, but not to limit the scope of the invention. Unless otherwise stated, all parts and percentages in the specification and claims are by weight.

EXAMPLE I

The reactor was charged with 42.0 g (0.20 moles) 3-hydroxymethyl-5-hydroxymethylthio-1,3,4-thiadiazolidine-2-thione, 45.6 g (0.20 moles) p,p'-isopropylidenediphenol, 150 ml toluene, and 0.50 g p-toluenesulfonic acid catalyst. The reaction mixture was refluxed for 1½ hours. Water, 7.2 g (0.40 moles) was removed by azeotropic distillation. After cooling to 90° C., toluene was stripped and the molten reaction product was removed. Upon cooling it became a brittle yellow solid. The yield of the copolymer was 76.5 g.

EXAMPLE II

The reactor was charged with 65.6 g (0.40 moles) 2-t-butyl-4-methylphenol, 30.0 g (0.20 moles) 3,5-dimercapto-1,3,4-thiadiazole, 32.4 g (0.40 moles) 37% aqueous solution of formaldehyde, 200 ml toluene, and 0.50 g p-toluenesulfonic acid catalyst. About 28.0 g (1.555 moles) water was collected by azeotropic distillation. The product was treated with 15 ml of 20% aqueous solution of sodium carbonate to remove unreacted catalyst and toluene was stripped. The product, 3-(2- hydroxy-3-t-butyl-4-methylbenzylthio)-1,3,4-thiadiazolidine-2-thione, was a yellowish brown solid weighing 97.5 g.

EXAMPLE III

Test specimens were prepared by compounding two batches of natural rubber with antioxidants of the invention and other conventional compounding ingredients. For each batch a sample containing no antioxidant was used as control. The samples were press cured for 15 minutes at 153° C. After 4 day aging in test tubes at 100° C., the elongation and tensile strength were determined according to ASTM D-412 method. The physical data compiled in Tables I and II showed that the specimens containing the compounds of the invention retained the desired properties under oxidative condtitions.

The above embodiments and illustrations have shown various aspects of the present invention. Other variations will be evident to those skilled in the art and such modifications are intended to be within the scope of the invention as defined in the appended claims.

TABLE I

| Ingredients | \multicolumn{5}{c}{Vulcanizates, parts by weight} |
|---|---|---|---|---|---|
|  | 1 | 2 | 3 | 4 | 5 |
| Smoked sheet rubber | 100.0 | 100.0 | 100.0 | 100.0 | 100.0 |
| K-STAY G[(1)] | 5.0 | 5.0 | 5.0 | 5.0 | 5.0 |
| Stearic acid | 2.0 | 2.0 | 2.0 | 2.0 | 2.0 |
| Zinc oxide | 5.0 | 5.0 | 5.0 | 5.0 | 5.0 |
| Carbon black | 50.0 | 50.0 | 50.0 | 50.0 | 50.0 |
| Sulfur | 2.5 | 2.5 | 2.5 | 2.5 | 2.5 |
| N—Oxydiethylene-2-benzothiazole-sulfenamide | 0.5 | 0.5 | 0.5 | 0.5 | 0.5 |
| 3-(2-Hydroxy-3-t-butyl-5-methylbenzyl)-5-(2-hydroxy-3-t-butyl-5-methylbenzylthio)-1,3,4-thiadiazolidine-2-thione | — | 2.0 | — | — | — |
| Copolymer of p,p'-isopropylidenediphenol and 3-hydroxymethyl-5-hydroxymethylthio 1,3,4-thiadiazolidine-2-thione (1:1) | — | — | 2.0 | — | — |
| Copolymer of p,p'-isopropylidenediphenol and 3-hydroxymethyl-5-hydroxymethylthio-1,3,4-thiadiazolidine-2-thione (2:1) | — | — | — | 2.0 | — |
| 3-(2,6-dihydroxy-3,5-di-t-butylbenzyl)-5-(2,6-dihydroxy-3,5-di-t-butylbenzylthio)-1,3,4-thiadiazolidine-2-thione | — | — | — | — | 2.0 |
| Physical properties after cure |  |  |  |  |  |
| Tensile, psi | 3420 | 3080 | 2210 | 2240 | 3280 |
| Elongation | 600 | 590 | 530 | 520 | 560 |
| Hardness | 57 | 58 | 56 | 58 | 57 |
| Physical properties after aging |  |  |  |  |  |
| Tensile, percent retained | 25 | 47 | 46 | 58 | 48 |
| Elongation, percent retained | 45 | 51 | 57 | 60 | 64 |
| Hardness, points changed | 0 | +7 | +3 | +2 | +3 |

[(1)]Rubber processing aid distributed by R. T. Vanderbilt Company, Inc.

TABLE II

| Ingredients | Vulcanizates, parts by weight | |
|---|---|---|
|  | 6 | 7 |
| Smoked sheet rubber | 100.0 | 100.0 |
| K-STAY G | 5.0 | 5.0 |
| Stearic acid | 2.0 | 2.0 |
| Zinc oxide | 5.0 | 5.0 |
| Carbon black | 50.0 | 50.0 |
| Sulfur | 2.5 | 2.5 |
| N—Oxydiethylene-2-benzothiazolesulfenamide | 0.5 | 0.5 |
| 3-(3,5-Di-t-butyl-4-hydroxybenzyl)-5-(3,5-di-t-butyl-4-hydroxybenzylthio)-1,3,4-thiadiazole-2-thione | — | 2.0 |
| Physical properties after cure |  |  |
| Tensile, psi | 3470 | 3550 |
| Elongation | 580 | 570 |
| Hardness | 58 | 60 |
| Physical properties after aging |  |  |
| Tensile, percent retained | 14 | 42 |
| Elongation, percent retained | 26 | 56 |
| Hardness, points changed | −4 | 0 |

What is claimed is:

1. A stabilized composition comprising natural rubber and about 0.2 to 5 parts per hundred parts rubber of a 1,3,4-thiadiazole compound of the structural formula

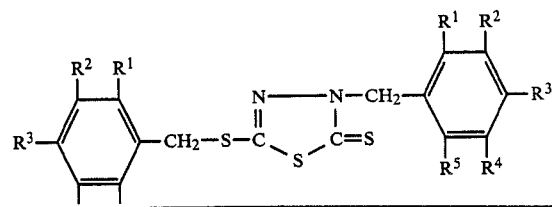

wherein $R^2$ represents t-butyl group, $R^4$ represents $C_{1-4}$-alkyl group, and $R^1$, $R^3$ and $R^5$ represents hydrogen and hydroxy groups provided that $R^1$ and $R^5$ are hydrogens when $R^3$ is hydroxy and $R^3$ is hydrogen when $R^1$ and $R^5$ are hydroxy groups.

2. A composition according to claim 1 wherein the 1,3,4-thiadiazole compound is 3-(2-hydroxy-3-t-butyl-5-methylbenzyl)-5-(2-hydroxy-3-t-butyl-5-methylbenzylthio-1,3,4-thiadiazolidine-2-thione.

3. A process for stabilizing rubber against oxidative degradation which comprises incorporating in the rubber about 0.2 to 5.0 parts per hundred parts rubber of a 1,3,4-thiadiazole compound of the structural formula

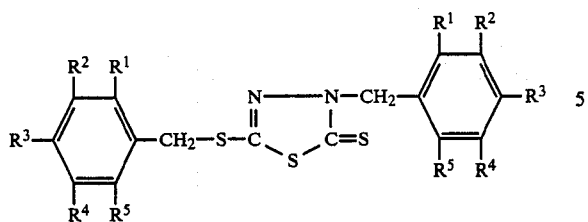
wherein $R^2$ represents t-butyl group, $R^4$ represents $C_{1-4}$-alkyl group, and $R^1$, $R^3$ and $R^5$ represent hydrogen and hydroxy groups provided that $R^1$ and $R^5$ are hydrogens when $R^3$ is hydroxy and $R^3$ is hydrogen when $R^1$ and $R^5$ are hydroxy groups.
* * * * *